US009155525B2

(12) United States Patent
Lipinsky et al.

(10) Patent No.: US 9,155,525 B2
(45) Date of Patent: Oct. 13, 2015

(54) URINE SAMPLE COLLECTION DEVICE

(71) Applicant: Lipinsky Enterprises, LLC, Minneapolis, MN (US)

(72) Inventors: Catherine Lipinsky, Minneapolis, MN (US); Thomas A. Wendt, Colfax, WI (US)

(73) Assignee: Lipinsky Enterprises, LLC, Minneapolis, MN (US)

( * ) Notice: Subject to any disclaimer, the term of this patent is extended or adjusted under 35 U.S.C. 154(b) by 0 days.

(21) Appl. No.: 14/209,254

(22) Filed: Mar. 13, 2014

(65) Prior Publication Data

US 2014/0276216 A1   Sep. 18, 2014

Related U.S. Application Data

(63) Continuation-in-part of application No. 13/815,859, filed on Mar. 15, 2013.

(51) Int. Cl.
| | |
|---|---|
| *A61B 5/00* | (2006.01) |
| *B65D 81/00* | (2006.01) |
| *A61B 10/00* | (2006.01) |
| *A61B 18/02* | (2006.01) |

(52) U.S. Cl.
CPC ....... *A61B 10/007* (2013.01); *A61B 2018/0212* (2013.01)

(58) Field of Classification Search
CPC ...................................................... A61B 5/00
USPC ................. 600/573, 574, 575, 576, 579, 580
See application file for complete search history.

(56) References Cited

U.S. PATENT DOCUMENTS

| | | | | |
|---|---|---|---|---|
| 3,571,817 | A | * | 3/1971 | Gosnell .......................... 4/144.1 |
| 3,635,091 | A | | 1/1972 | Linzer et al. |
| 3,811,136 | A | | 5/1974 | Whitney et al. |
| 4,203,169 | A | | 5/1980 | Dale |
| 4,276,889 | A | * | 7/1981 | Kuntz et al. ................... 600/574 |
| 4,331,162 | A | * | 5/1982 | Kuntz et al. ................... 600/574 |
| 4,554,687 | A | * | 11/1985 | Carter et al. ................... 4/144.2 |
| 4,557,274 | A | | 12/1985 | Cawood |
| 4,569,090 | A | * | 2/1986 | Muller ............................ 4/144.2 |
| 5,146,637 | A | * | 9/1992 | Bressler et al. ................... 4/445 |
| 5,285,540 | A | * | 2/1994 | Putz ................................ 4/661 |

(Continued)

OTHER PUBLICATIONS

S. Collier, F. Matjiu, G. Jones, M. Harbor & S. Hopkins, "A Prospective Study Comparing Contamination Rates Between a Novel Mid-Stream Urine Collection Device (Peezy) and a Standard Method in Renal Patients," J. Clinical Pathology, vol. 0, pp. 1-4 (2013).

(Continued)

*Primary Examiner* — Rene Towa
*Assistant Examiner* — May Abouelela
(74) *Attorney, Agent, or Firm* — Moss & Barnett (57) ABSTRACT

A urine sample collection device having a collection vessel for capturing urine from a patient, and an associated sample collection container portion for gathering the urine sample in an assured manner without the need for manual transfer. The urine sample collection device can be easily mounted inside a toilet bowl, so that the patient can deliver the urine stream to the toilet in the normal manner to produce the urine sample. The device avoids splashes of residual urine after the sample container is remove from the collection vessel, and a urine flow barrier shield for automatically accommodating the clean-catch method for delivering a urine sample.

18 Claims, 9 Drawing Sheets

(56) References Cited

U.S. PATENT DOCUMENTS

| | | | |
|---|---|---|---|
| 5,422,076 A * | 6/1995 | Jones | 600/574 |
| 5,592,699 A * | 1/1997 | Jensen | 4/144.3 |
| 6,079,057 A * | 6/2000 | Mette | 4/342 |
| 6,151,972 A * | 11/2000 | Venter et al. | 73/863.41 |
| 6,163,892 A * | 12/2000 | Abbato | 4/144.1 |
| 6,212,698 B1 | 4/2001 | Stingley et al. | |
| 6,358,477 B1 * | 3/2002 | Webb et al. | 422/557 |
| 6,775,852 B1 | 8/2004 | Alvarez et al. | |
| 6,811,754 B2 * | 11/2004 | House | 422/557 |
| 7,798,907 B2 * | 9/2010 | Piccionelli et al. | 463/49 |
| 7,819,821 B2 | 10/2010 | Forte et al. | |
| 7,871,385 B2 | 1/2011 | Levinson | |
| 8,043,272 B2 * | 10/2011 | Long et al. | 604/385.01 |
| 8,079,562 B1 | 12/2011 | Denman | |
| 8,328,733 B2 | 12/2012 | Forte et al. | |
| 8,613,711 B2 * | 12/2013 | Babcock | 600/562 |
| 8,690,794 B1 * | 4/2014 | Gallardo | 600/562 |
| 2004/0003457 A1 | 1/2004 | Renda | |
| 2004/0241052 A1 | 12/2004 | House | |
| 2005/0177937 A1 | 8/2005 | Kneese et al. | |
| 2005/0193482 A1 | 9/2005 | Gambla et al. | |
| 2008/0183102 A1 * | 7/2008 | Dunkin | 600/580 |
| 2009/0082745 A1 * | 3/2009 | Ying et al. | 604/367 |
| 2013/0053729 A1 | 2/2013 | Stevic-Wages et al. | |
| 2013/0296739 A1 * | 11/2013 | Schultz | 600/573 |
| 2014/0276214 A1 * | 9/2014 | Lipinsky et al. | 600/573 |
| 2015/0051510 A1 * | 2/2015 | Husmark et al. | 600/573 |

OTHER PUBLICATIONS

H.A. Cohen, B. Woloch, N. Linder, A. Vardi, A. Barzilai, "Urine Samples from Disposable Diapers: an Accurate Method for Urine Cultures," J. Fam Pract. vol. 44(3), pp. 290-292 (Mar. 1997).

Charlwood Design, "Mittstrom Mid Stream Urine Device" [Retrieved from the internet: http://charlwood.com.au/mittstrom-mid-stream-urine-device/].

JBOL Ltd. (Oxford, UK), "CleanCatch® Midstream Urine Collection Device," NHS Purchasing and Supply Agency, Centre for Evidence-Based Purchasing (CEP) 07004; (Jan. 2008).

* cited by examiner

URINE SAMPLE COLLECTION DEVICE

CROSS-REFERENCE TO RELATED APPLICATIONS

This application is a continuation-in-part of U.S. Ser. No. 13/815,859 filed on Mar. 15, 2013 entitled "Urine Sample Collection Device," which is hereby incorporated by reference.

FIELD OF THE INVENTION

This invention relates generally to the collection of urine samples used for chemical and microscopic urine laboratory analysis pursuant to medical or compliance diagnostic testing, and more specifically to a toilet-mounted device that automatically collects into a collection container a urine sample produced by a person urinating into the toilet, while maintaining the purity of the collected sample and cleanliness of the sample container.

BACKGROUND OF THE INVENTION

Urination is a process by which a human naturally expels urine from the body that contains byproduct of cellular metabolism rich in nitrogen that require elimination from the bloodstream. Urine principally contains water, but also includes an assortment of inorganic salts and organic compounds, including proteins, hormones, and a wide range of metabolites that vary by what was put into the body. Urination represents the primary method for excreting these water-soluble chemicals from the body.

These chemicals, along with the presence of unwanted bacteria, can be detected and analyzed by urinalysis. Doctors order urine tests for patients to make sure that the kidneys and certain other organs are functioning properly, or when they suspect that the patient might have an infection in the kidneys, bladder, or other parts of the urinary tract. The kidneys make urine as they filter wastes from the bloodstream, while leaving substances in the blood needed by the body like proteins and glucose. But if the urine contains glucose, too much protein, or has other irregularities, it may constitute a sign of a health problem or disease.

A urinalysis test can measure the number and variety of red and white blood cells, the presence of bacteria and other organisms, the presence of substances like glucose that should not be found in urine, the pH which shows how acidic or basic the urine is, and the concentration of the urine. The doctor or a laboratory will typically place a dipstick in the urine whose patches change color to indicate things like the presence of white or red blood cells or glucose. The doctor or laboratory will also usually examine the urine under a microscope to check for other substances like bacteria that indicate different health conditions.

But, it can be difficult to collect a urine sample from a child or the elderly or disabled patient to analyze. Acute urinary tract infections ("UTI") are relatively common in children. Children younger than three years of age are not usually toilet trained yet, so a urine sample will typically be collected from their soiled diaper. Children of ages 3-10 years will usually be toilet trained, but they can be embarrassed by or fearful of the process in the doctor's office, and experience difficulty in urinating upon demand. Moreover, children of ages 3-5 years, older children with severe disabilities, and adults who have difficulty seeing, difficulty with dexterity (implied by having issues with walking and grasping), or a mental disability that may preclude full understanding and execution of a task can also have trouble with the mechanics required for urinating a sample directly into a collection container. It is estimated that 44.8 million children, disabled, and elderly persons in the United States may face these challenges in providing urine samples.

Furthermore, the skin surrounding the urinary opening of the male penis and female vagina is normally home to some of the same bacteria that causes infections in the urinary tract. If these bacteria contaminate the urine sample during the collection process, the doctor may be unable to process the sample to determine whether or not there is a true infection in the patient. Thus, the patient will be required in a "clean catch" process to clean and rinse the skin surrounding the urinary opening in the body, then urinate to expel any bacteria-laden urine, then stop momentarily, and finally urinate again the 1-2 ounce sample into the collection container. Catching this urine sample in "mid-stream" can require unusual coordination and manual dexterity for a child, or disabled or elderly patient.

Various devices have been developed and used over time to assist a patient with providing a urine sample. For example, U.S. Pat. No. 3,811,136 issued to Whitney et al. provides a hand-held urine specimen collection container consisting of a funnel screwed into a collection bottle. The urine is collected by the funnel portion and delivered by gravity into the bottle. U.S. Published Application 2004/0003457 filed by Renda constitutes a portable urinal having a funnel positioned on top of a hand-held base container. But both of these devices must be held and manipulated by the patient with the risk of spillage or contamination of the collected urine sample.

U.S. Pat. No. 5,920,916 issued to Norton discloses a rigid, saddle-shaped funnel that can be manually fitted against the female pelvis. Like a bed pan, it collects urine for delivery to a screwed-on collection vessel. But, the urine collected in this vessel must then be transferred to a collection container by the patient or assistant.

Another common type of urine collection device is mounted inside a toilet bowl. A patient can simply urinate into the toilet in a normal fashion, and the urine sample will fall into some type of container. This type of toilet-mounted urine collection container comes in various designs. For example, U.S. Pat. No. 3,571,817 issued to Gosnell discloses a urine collection bag mounted to the rim of the toilet bowl with the bag suspended into the bowl. The urine must be manually transferred from the bag to another container. U.S. Pat. No. 8,079,562 issued to Denmar discloses a stand-alone urine collection container set onto a bracket mounted onto the toilet bowl. However, the patient must be able to direct the urine flow directly into the container, which can be difficult for female and child patients. U.S. Pat. No. 6,811,754 issued to House, and U.S. Published Application 2004/0241052 filed by House show urine collection cups mounted into the bottom of a rigid collection vessel. U.S. Pat. No. 6,775,852 issued to Alvarez et al. illustrates a urine collection cup held by a flexible bag that is set into the toilet bowl with an elastomeric band at its top secured around the toilet bowl. In all of these cases, the cup will be splashed with urine, and therefore unpleasant for the doctor's assistant to handle.

U.S. Pat. No. 6,358,477 issued to Webb et al. illustrates another design for a "funnel" made from a flexible sheet that is attached to the toilet seat with a collection cup secured to the sheeting by adhesive. U.S. Pat. No. 6,212,698 issued to Stingley et al. discloses a flexible mounting strip positioned on top of the toilet bowl rim. A collection cup is suspended from the bottom of the bag. Once again, the collection cup will be splashed with urine.

U.S. Pat. No. 6,151,972 issued to Venter et al. teaches a rigid molded plastic trough that is clipped to the toilet bowl rim, and suspends a collection cup from its bottom. U.S. Pat. No. 5,146,637 issued to Bressler et al. discloses a rigid plastic funnel that specifically fits into the opening of the toilet bowl with a collection cup suspended from an opening in its bottom.

But, all of these funnel-like devices mounted to toilet bowls suffer from a number of disadvantages. They require complicated mounting rods or brackets that must be manipulated to secure the device to and remove it from the toilet. A flexible sheeting may tear, thereby losing the urine sample into the toilet bowl. A simple cup set onto a mounting bracket may fail to catch the urine sample. The collection cup may be splattered by urine and therefore messy to handle. The urine collected in the cup can become contaminated by bacteria, thereby interfering with the validity of the urinalysis results.

Moreover, none of these urine collection devices used in the medical industry allow for the patient to practice the accepted "clean catch" mid-stream collection process for providing a urine sample free of bacteria contamination. The patient must pass the initial short burst of urine into the toilet, get off the toilet while the urine collection contraption is mounted to the toilet bowl, and then get back onto the toilet to provide the urine specimen. The physical coordination and lack of privacy required by such a process will interfere with the collection of urine samples from patients in many cases.

There are some prior art urine collection devices that purport to accommodate the clean-catch mid-stream urine sample collection process. For example, a "Peezy" collection device is disclosed in S. Collier, F. Matjiu, G. Jones, M. Harbor & S. Hopkins, "A Prospective Study Comparing Contamination Rates Between a Novel Mid-Stream Urine Collection Device (Peezy) and a Standard Method in Renal Patients," *J. Clinical Pathology*, vol. 0, pp. 1-4 (2013). The Peezy device incorporates a sponge inserted into a funnel mounted to the top of the collection container. The device is placed in a toilet bowl under the perineum of the patient who allows the urine to flow into the funnel. The urine passes through the device, and the cellulose sponge expands as the first 10-15 ml of urine is passed by the patient. The urine is then forced into the sample container. Any overflow from this funnel and container passes into the toilet. But, the bacteria-laden initial urine flow captured by the sponge can contaminate the subsequent mid-stream urine flow that passes through the same sponge. This defeats the purpose of the clean-catch mid-stream urine collection method. Not surprisingly, the researchers discovered that the Peezy device actually increased the rate of the epithelial cells and mixed growths found in the urine samples when compared against the counts found in the samples collected directly by the conventional clean-catch mid-stream collection process.

A Mittstrom mid-stream urine collection device designed by Charlwood entails a corn starch membrane that covers the sample container held suspended in a toilet bowl by a corn starch saddle. When a patient passes urine, the first three seconds of flow is absorbed by the corn starch membrane and dissolves it, thereby allowing the subsequent urine flow to pass directly into the sample container. But, the dissolved, bacteria-laden membrane can contaminate the mid-stream flow to render the urine sample unreliable for diagnostic testing.

The clean-catch midstream device manufactured and sold by JBOL Ltd. of Oxford, England in the United Kingdom employs a mechanical approach in which air released from the sample container mounted to the device forces the initial urine stream to flow up and out of the container, while the subsequent mid-stream urine flows into the container. But, this "channeling feature" still appears to allow the contaminated initial urine flow to contact the mid-stream urine flow or the sample container. Thus, while the process employed by this particular device may be relatively automatic, it can result in a bacterially contaminated urine sample.

U.S. Pat. No. 7,798,907 issued to Piccionelli et al., Renda, and U.S. Published Application 2005/0177937 filed by Kneese et al. disclose various floating targets and heat or moisture-activated materials useful for encouraging young children to learn to use the toilet. But none of the devices provide any kind of functionality for collecting urine samples, especially via the clean catch process.

A urine sample collection device that can be easily mounted to a toilet bowl having a collection vessel for capturing urine from a patient, and an associated sample collection container portion for gathering the urine sample in an assured manner without the need for manual transfer, while maintaining the integrity and purity of the sample would be beneficial. Moreover, the ability to remove the sample collection container with the urine sample inside from the collection vessel without splashed urine deposits or other mess on the container would also be helpful. Furthermore, the urine sample collection device should collect the mid-stream urine sample after automatically diverting the initial bacteria-laden urine to enable the patient to employ the clean-catch method during delivery of urine to avoid introduction of bacteria from around the urinary opening of the patient's body into the sample. Such a device would greatly facilitate the process for obtaining urine samples from children and elderly or physically infirm patients, while enhancing their sense of independence, privacy, and human dignity in not having a medical assistant intrusively present to assist them with the urine sample collection process.

SUMMARY OF THE INVENTION

A urine sample collection device having a collection vessel for capturing urine from a patient, and an associated sample collection container portion for gathering the urine sample in an assured manner without the need for manual transfer is provided by this invention. The urine sample collection device can be easily mounted inside a toilet bowl, so that the patient can deliver the urine stream to the toilet in the normal manner to produce the urine sample. The collection vessel portion of the urine sample collection device is designed with an anti-splash means in the form, e.g., of an overflow outlet, outlet valve, or siphon tube to ensure that there is no excess volume of urine in the collection vessel as the sample collection container is removed to prevent urine from splashing on the sample collection container or medical assistant. The urine sample collection device of the present invention maintains the integrity and purity of the sample as it is automatically transferred from the collection vessel to the sample collection container. Moreover, it preferably includes a urine flow barrier shield positioned across the top opening of the collection vessel that retains the initial urine volume that might contain bacteria delivered by the patient during a clean-catch mid-stream collection method, while automatically removing itself thereafter so that the subsequent mid-stream volume of urine delivered by the patient can flow into the collection vessel and sample collection container free of bacterial taint. This enables the patient to deliver urine to the collection vessel using the clean-catch method to avoid introduction of bacteria from around the urinary opening of the patient's body into the resulting sample. The urine sample collection device can be readily removed from the toilet bowl by raising the toilet seat to which it is mounted. This avoids the need for manually dismounting the device from the toilet in order to remove the sample container from the collection vessel. Such a urine sample collection device greatly facilitates the process for obtaining urine samples from children or disabled or elderly patients, while enhancing their sense of independence, privacy, and human dignity in not having a medical assistant intrusively present to assist them with the urine sample collection process. It also reduces the incidence of false positive urinalysis results for bacterial strains that can lead to the over-prescription of antibiotic drugs, and the development over time of antibiotic-resistant bacterial strains which constitutes a public health risk.

DETAILED DESCRIPTION OF THE PREFERRED EMBODIMENT

A urine sample collection device having a collection vessel for capturing urine from a patient, and an associated sample collection container portion for gathering the urine sample in an assured manner without the need for manual transfer is provided by this invention. The urine sample collection device can be easily mounted inside a toilet bowl, so that the patient can deliver the urine stream to the toilet in the normal manner to produce the urine sample. The collection vessel portion of the urine sample collection device is designed with an overflow outlet, outlet valve, or siphon tube to ensure that there is no excess volume of urine in the collection vessel as the sample collection container is removed to prevent urine from splashing on the sample collection container or medical assistant. The urine sample collection device of the present invention maintains the integrity and purity of the sample as it is automatically transferred from the collection vessel to the sample collection container. Moreover, it enables the patient to deliver urine to the collection vessel using the clean-catch mid-stream collection method to avoid introduction of bacteria from around the urinary opening of the patient's body into the resulting sample. Such a urine sample collection device greatly facilitates the process for obtaining urine samples from children or disabled or elderly patients, while enhancing their sense of independence, privacy, and human dignity in not having a medical assistant intrusively present to assist them with the urine sample collection process. It also reduces the incidence of false positive urinalysis results for bacterial strains that can lead to the over-prescription of antibiotic drugs, and the development over time of antibiotic-resistant bacterial strains which constitutes a public health risk.

As used within this Application, "patient" means a person from whom a urine sample is sought for medical or compliance purposes, particularly a child or a disabled or elderly person, so a urinalysis test can be performed.

Figure 1:
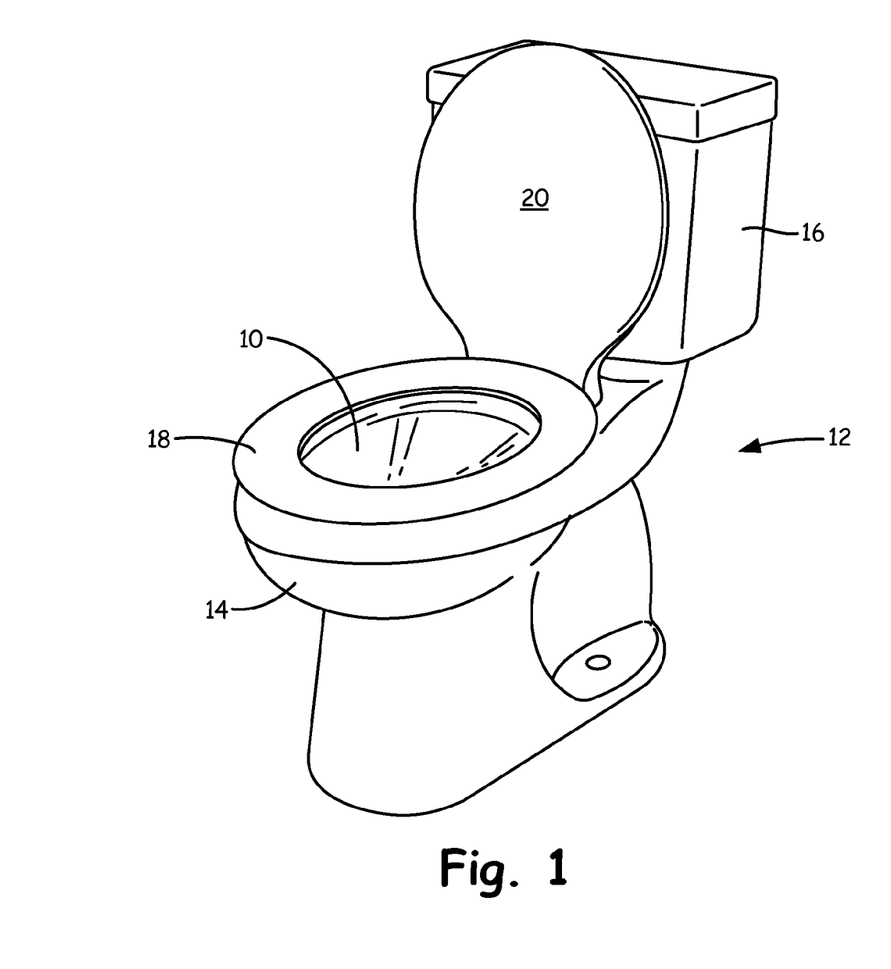
FIG. 1 represents a perspective view of the urine sample collection device of the present invention mounted inside a toilet bowl with the seat in the down position.

The urine sample collection device 10 of the present invention is shown in FIG. 1 in association with a conventional toilet 12. Toilet 12 comprises a bowl 14, water supply tank 16, seat 18, and lid 20 in the normal manner. A patient sitting on seat 18 or standing up with the lid 20 in the opened position can deliver a stream of urine into bowl 14, whereupon it is evacuated from the bowl with a flush of water provided by water supply tank 16.

Urine sample collection device 10 is mounted to the toilet 12, so that it extends down into bowl 14 where it can collect the urine stream emitted by the patient. As seen more clearly in FIG. 2, this urine sample collection device 10 is preferably secured to the bottom surface of seat 18, so that when the seat is raised, the urine sample collection device is lifted out of toilet bowl 14.

Figure 2:
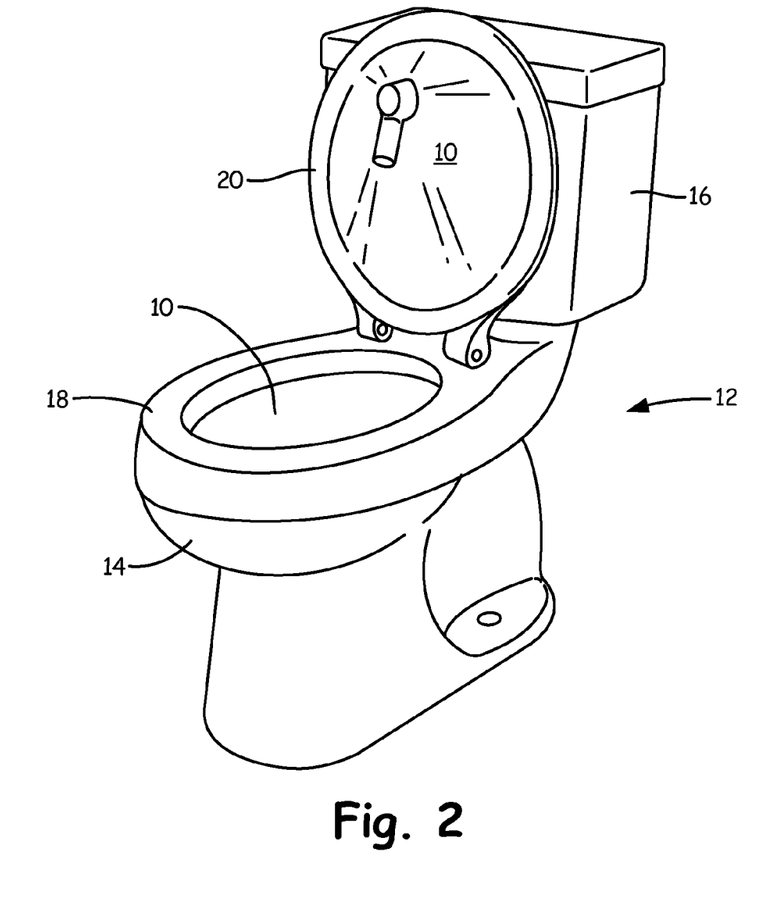
FIG. 2 represents a perspective view of the urine sample collection device of FIG. 1 removed from the toilet bowl by the raised toilet seat.
Figure 3:
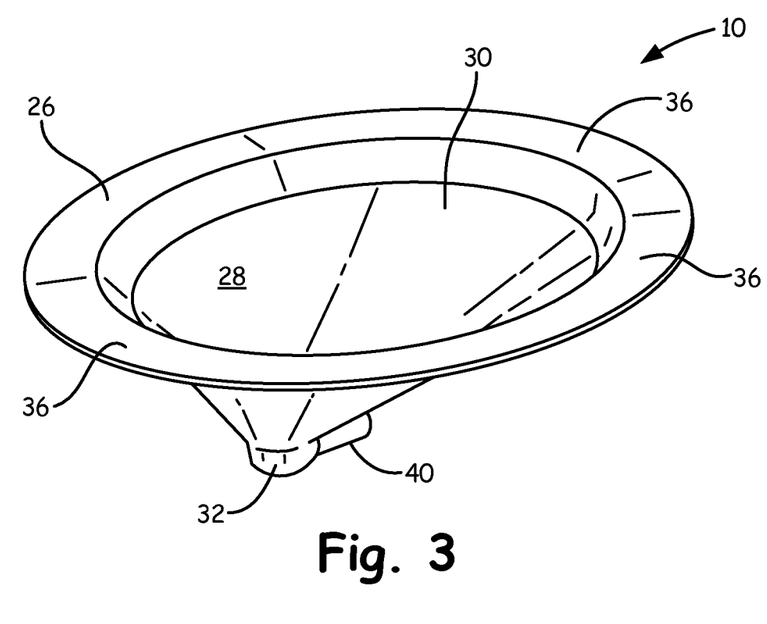
FIG. 3 represents a perspective view of the urine sample collection device.
Figure 4:
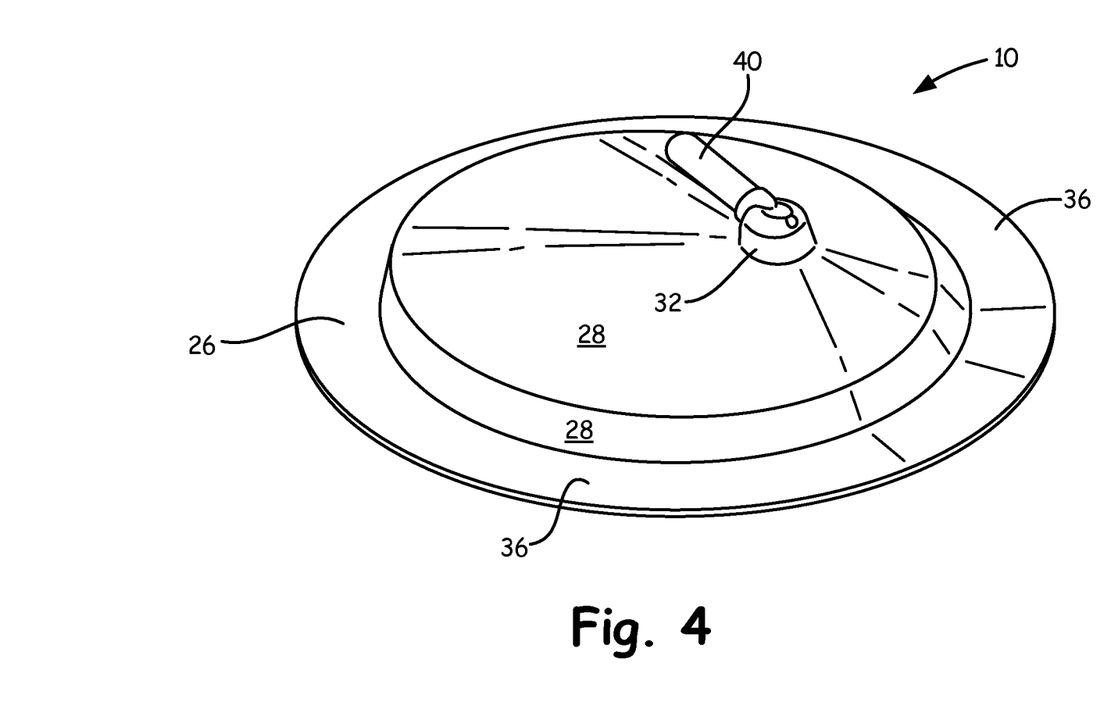
FIG. 4 represents a perspective view of the bottom of the urine sample collection device.
Figures 5, 6:
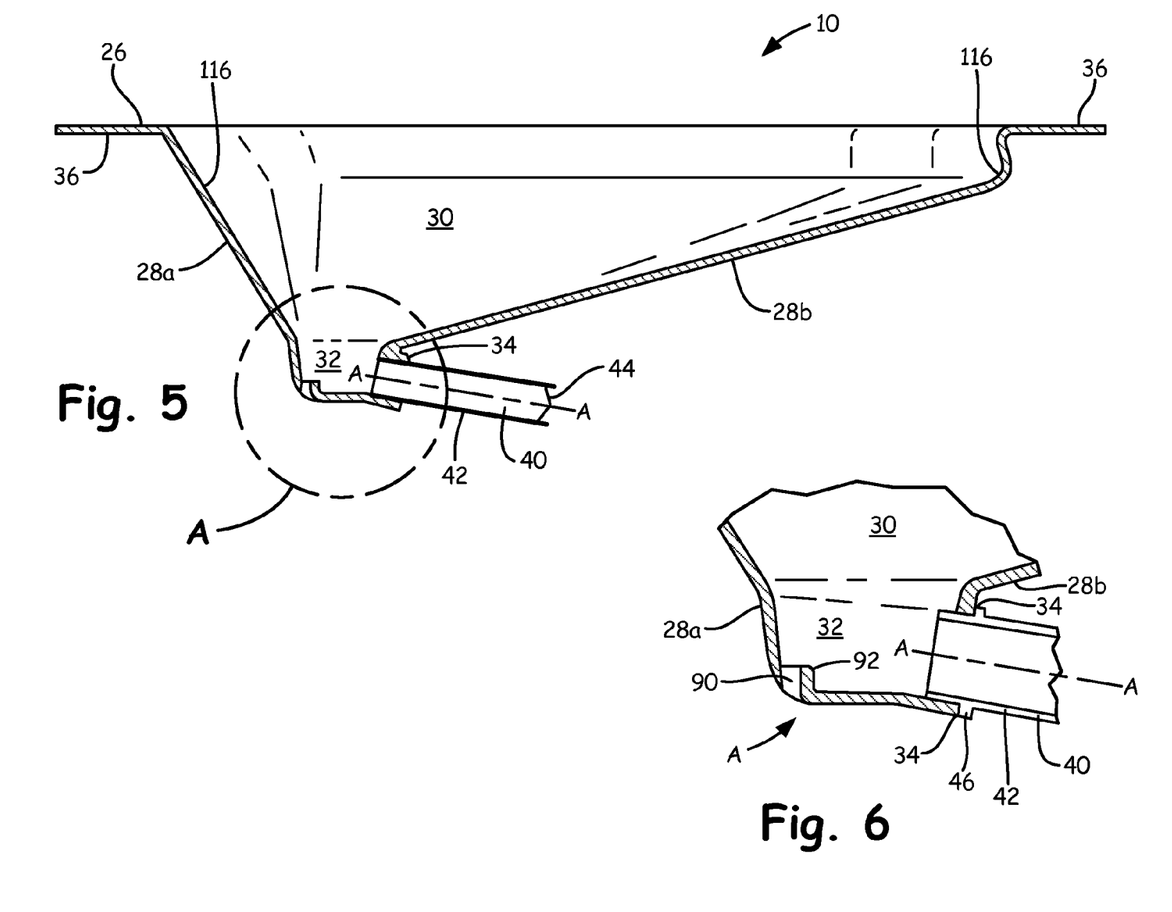
FIG. 5 represents a side cut-away view of the urine sample collection device.
FIG. 6 represents an enlarged view of the portion of the urine sample collection device of FIG. 5 inside circle A.

Urine sample collection device 10 is shown independent of toilet 12 in FIGS. 3-5. The device comprises a collection vessel 26 and a sample collection container 40 operatively connected to its lower end. Collection vessel 26 is bowl-shaped having side walls 28 defining an upper chamber 30 and a bottom well 32 with an outlet port 34 formed therein. Extending laterally from the perimeter of the top of side walls 28 is flanged lip 36. Collection vessel 26 should be sized, so that it fills substantially all of the opening of toilet bowl 14 with flanged lip 36 resting on the top of the toilet bowl to secure the collection vessel 26 in a suspended manner inside the upper portion of the toilet bowl so that it can catch the urine stream emitted by the patient into toilet 12. Alternatively, a plurality of adhesive strips 37 or other suitable securement means affixed to the top surface of flanged lip 36 can be used to attached collection vessel 26 to the bottom surface of toilet seat 18, as shown in FIG. 2. While this arrangement still permits collection vessel 26 to be suspended into toilet bowl 14, it can be easily removed from the toilet bowl simply by raising the toilet seat 18.

Collection vessel 26 may adopt any three-dimensional shape that is suitable for the volume of the toilet bowl 14. For example, it may feature a round or oval opening at its top defined by flanged lip 36 with uniform side walls 28. Alternatively, it may feature non-uniform side walls with a more-steeply-sloped front wall 28a and a more-gently-sloped back wall 28b, as depicted in FIG. 5. As a urine stream emitted by the patient falls into upper chamber 30 of collection vessel 26, some of it will flow directly into bottom well 32. Another portion of it will hit more-steeply-sloped front wall 28a whereupon it will flow laterally along the wall down into bottom well 32. Another portion of the urine stream will hit more-gently-sloped back wall 28b whereupon it will flow laterally along the wall down into bottom well 32.

Figure 7:
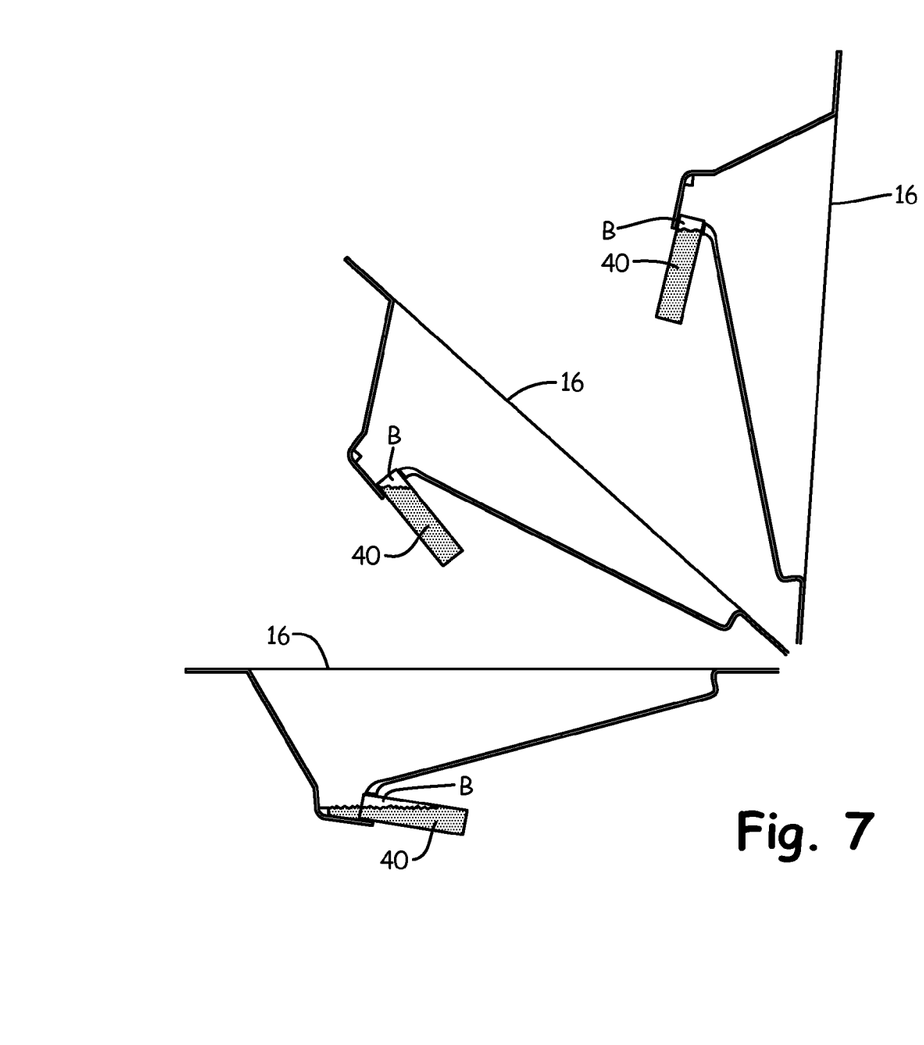
FIG. 7 represents a multiple-stage view of the urine sample collection device being raised out of the toilet bowl with a urine sample contained inside the sample collection container.

Collection vessel 26 is preferably shaped so that it may be mounted in an orientation inside the toilet bowl 14 with more-steeply-sloped front wall 28b towards the front of the toilet bowl. Two principal advantages are provided by this arrangement. First, the more-gently-sloped back wall of the collection vessel allows the bottom well to be moved closer to the front of the vessel, which is ideal for female patients, as well as male patient sitting on the toilet to provide a urine sample. At the same time, when a male patient is standing in front of toilet 12 to urinate into the collection vessel 26, the urine will strike the more-gently-sloped back wall 28b to avoid splashing. Second, this arrangement with sample collection container 40 mounted to the rear of bottom well 32 ensures that when the urine sample collection device 10 is lifted out of the toilet bowl 14 by means of raising the toilet seat 18 (see FIG. 7), the sample container 40 will be upright to securely hold the urine sample contained therein.

Urine settled inside bottom well 32 will flow by means of gravity into sample collection container 40. As shown more clearly in FIG. 5, sample collection container 40 is cylindrically-shaped, although it may adopt any other suitable shape. It comprises side wall 42 and bottom wall 44, defining longitudinal axis A-A. Flange 36 extends around the outside perimeter of side wall 42 near the open end of the sample collection container.

While the sample collection container 40 can be mounted to the bottom of collection vessel 26, it preferably is mounted to outlet port 34 disposed along the bottom portion of side wall 28b, as shown more clearly in FIG. 5. There are many means in which this sample collection container 40 can be secured to the bottom well. For example, the dimensions of the circumference of sample collection container 40 and outlet port 34 may be closely matched to enable the sample container to be snap fitted into engagement with the outlet port. Alternatively, male threads 50 (not shown) formed along the exterior of side walls 42 of the sample collection container 40 can mate with female threads 52 (not shown) formed in side wall 28b along the perimeter of outlet port 34. In this manner, sample collection container 40 can be screwably attached to collection vessel 26 so that urine delivered by the patient into the collection vessel readily flows down into sample collection container 40.

As shown in FIG. 5, the longitudinal axis A-A of sample collection container 40 may be downwardly sloped with respect to bottom well 32 in collection vessel 26, so that the urine more readily flows from bottom well 32 into sample collection container 40. In this manner, after the patient delivers a urine flow to the collection vessel 26 of urine sample collection device 10 and it flows into sample collection container 40, a medical assistant can remove the device from the toilet bowl 14 by lifting seat 18 (see FIGS. 2 and 7). Sample collection container 40 can then be unscrewed from outlet port 34 of collection vessel 26 and removed to provide a container for storing the resulting urine sample for subsequent urinalysis. This represents a marked improvement over other urine collection systems used in the industry where the entire urine collection system must be manually lifted outside the toilet bowl to provide access to the sample container. Instead, the sample collection device container 40 of the present invention can be quickly and conveniently removed from the collection vessel 26 when the urine sample collection device 10 is lifted out of the toilet bowl by the raised toilet seat without any need to dismount the device from the toilet.

Because of the structure of the collection vessel 26 with respect to the sample collection container 40, urine falling into the collection vessel 26 is guaranteed to flow into the sample collection container without the need for a medical assistant to manually pour a urine sample from the collection vessel into a separate sample container, as is commonly practiced within the medical industry. This helps to protect the integrity of the urine sample, since once sample collection container 40 is removed from collection vessel 26, it simply needs to be capped and labeled by the medical assistant for the patient. There will be less of a chance of getting urine samples confused between patients as can happen during manual transfer processes. Moreover, because the urine sample is automatically delivered to the sample collection container 40 by the urine sample collection device 10 of the present invention, there is less opportunity for contaminants to be introduced into the sample container by the patient or medical assistant, as also can readily occur during a manual transfer of a urine sample to a container. This will improve the integrity of any urinalysis tests conducted on the urine sample. A cap for the sample collection container can be removably secured to the bottom or side wall of the collection vessel, so that it is readily available to the medical assistant for immediate closure of the sample collection container holding the urine sample after the container has been removed from the collection vessel. This improves the integrity of the urine sample by protecting it from external contamination or accidental spillage.

Figure 8:
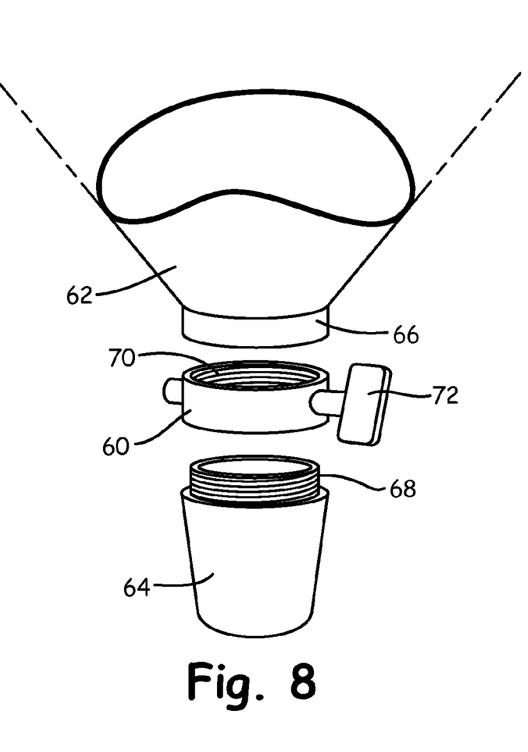
FIG. 8 represents an embodiment of the urine anti-splash means of the urine sample collection device comprising a shut-off valve disposed between the collection vessel and sample collection container.

Another important consideration for the medical assistant is to avoid handling a sample container that has urine splashed on its outside walls, or to have one's hands splashed with urine when the sample container 40 is removed from the collection vessel 26. As shown in FIG. 8, anti-splash means may comprise a valve housing 60 disposed between the collection vessel 62 and sample collection container 64. As shown in this embodiment, valve housing 60 may be secured to an annular lip 66 disposed along the bottom of collection vessel 62. Meanwhile, male threads 68 disposed along the exterior wall of sample collection container 64 mate with female threads 70 disposed along the interior wall of valve housing 60, so that sample container 64 can be screwably secured to valve housing 60. Valve housing 60 has knob 72 in the open position while the urine is delivered by the patient into the collection vessel 62, through the open valve housing, and down into sample collection container 64. Once the urine flow ceases, a medical assistant can simply turn knob 72 to its closed position to close valve 60. In this manner, any urine contained inside collection vessel 62 remains there while sample collection container 64 is removed from the closed valve housing, so that the urine cannot splash onto the hands of the medical assistant or floor or other surface. It is important, however, to make sure that the valve mechanism inside valve housing 60 is very close to the bottom of the valve housing to minimize any volume of urine contained inside the valve housing that can flow downwards once the sample collection container 64 is removed from the valve housing.

Figure 9:
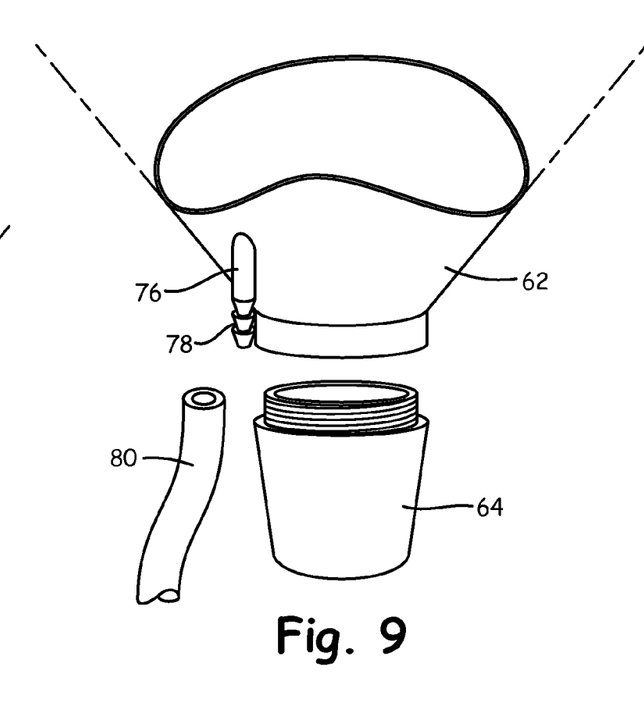
FIG. 9 represents an embodiment of the urine anti-splash means of the urine sample collection device comprising a siphon hose extending off the collection vessel.

Another possible embodiment for the anti-splash means is shown in FIG. 9. No valve housing 60 is present in this embodiment. Instead, outlet tube 76 formed along the side wall of collection vessel 62 extends downwardly to allow excess urine contained in the collection vessel above sample collection container 64 to flow out of the collection vessel 62. A siphon tube 80 is attached at its upper end to the outlet tube 76 with its lower end extending down into toilet bowl 14 outside of the urine sample collection device 10. A partial vacuum condition inside the siphon tube 80 will interact with the atmospheric pressure condition inside the collection vessel 62 to cause the excess urine contained inside the collection vessel to flow out through the siphon tube 80. In this manner, the urine will not splash out of the collection vessel 62 when the sample collection container 64 is removed.

A preferred embodiment of the anti-splash means is shown in FIGS. 5-6. Overflow outlet 90 is formed in the bottom wall of collection vessel 26 with vertical wall 92 separating it from bottom well 32. This overflow outlet 90 need only be about ⅛-inch in diameter. Vertical wall 92 should preferably extend along about ⅔ of the diameter of the sample collection container 40 mounted to the collection vessel 26. As the urine flows down through the collection vessel 26 into bottom well 32, it will flow through outlet port 34 into sample collection container 40. But, as the volume of available urine builds up in bottom well 32, it will flow over the top of vertical wall 92, whereupon it flows down through overflow outlet 90 from the collection vessel 26 into toilet bowl 14. This will ensure that too much urine does not build up inside the bottom well 32. When toilet seat 18 is raised to remove the urine sample collection device 10 from the toilet bowl (see FIG. 7), any residual urine contained in the bottom well 32 will flow into the sample collection container 40. In this manner, there will be no urine contained inside the collection vessel 26 to splash out when the sample collection container 40 is removed from the collection vessel 26. It is important that the open air volume B inside the sample collection container be slightly greater than the volume of bottom well 32 to ensure that when the urine sample collection device 10 is tipped up the sample collection container 40 is removed, there is no residual urine in the bottom well that cannot flow into the sample collection container 40. The overflow outlet 90 and vertical wall 92 act in combination to remove enough urine during the collection process inside the collection vessel 26 to make sure that the volume of urine contained inside the bottom well 32 is less than the available open air volume B inside the sample collection container.

The urine sample collection container 40 will typically be sourced from an industry supplier. These sample containers are widely available, and come in 10, 30, 50, and 60 ml volumes. Sixty milliliters corresponds to two ounces, which is adequate for most urinalysis test sample requirements. These sample containers typically are ½ inch in diameter. The ten milliliter-volume container is preferred for many urinalysis tests where larger volumes of urine are not required, or for, e.g., children who may have difficulty providing larger urine volumes.

Another important aspect of the urine sample collection device 10 of the present invention is its ability to accommodate the clean-catch mid-stream collection method that the medical industry wants patients delivering urine samples to practice to avoid contamination of the sample with any bacteria that may surround the urinary outlet of the patient's body. This is crucial for urinalysis tests directed to urinary tract infections, which are bacterial in cause, since bacteria from the urinary outlet that gets transferred to the urine sample may provide a false positive reading during the urinalysis test. None of the urine sample collection systems disclosed within the prior art accommodate such a clean-catch mid-stream method for collecting the urine from the patient without risking contamination of the resulting urine sample. This means that a patient must be carefully instructed by the medical assistant to start to urinate into the toilet to pass any bacteria from the urinary outlet into the toilet bowl, followed by urination of a sample into a collection container. These mechanics and timing can be very difficult for children, as well as disabled or elderly patients to perform.

Figure 10:
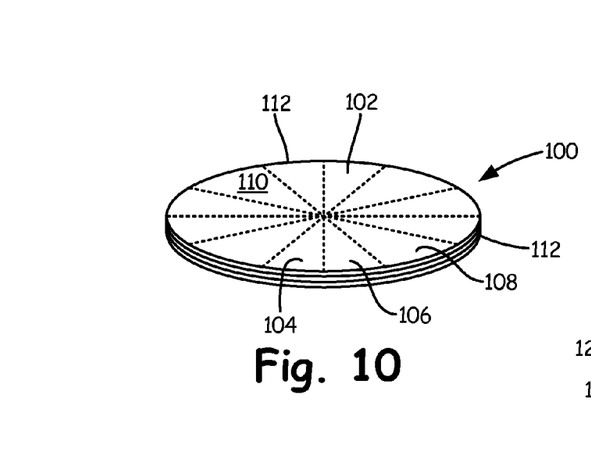
FIG. 10 represents a perspective view of the multiple-ply urine flow barrier shield for inside the collection vessel that adds clean-catch mid-stream collection process functionality to the urine sample collection device of the present invention.
Figure 11:
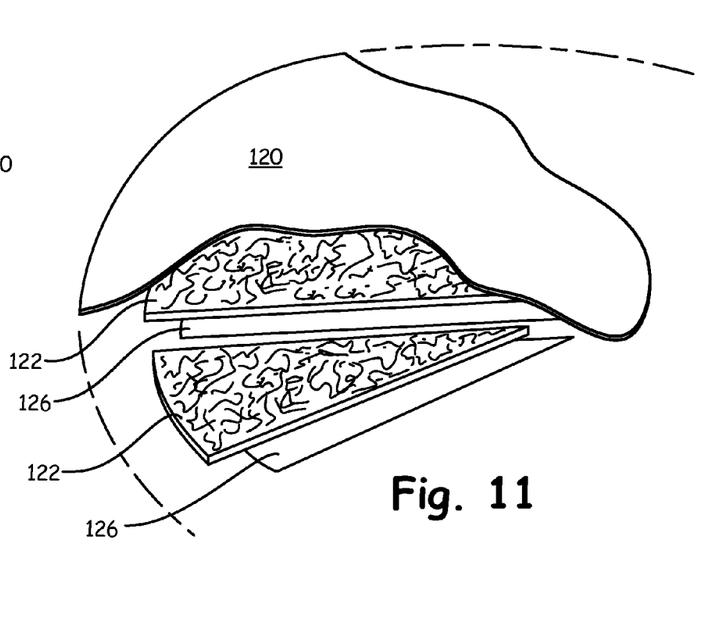
FIG. 11 represents a cut-away perspective view of a portion of the urine flow barrier shield of FIG. 10.
Figure 12:
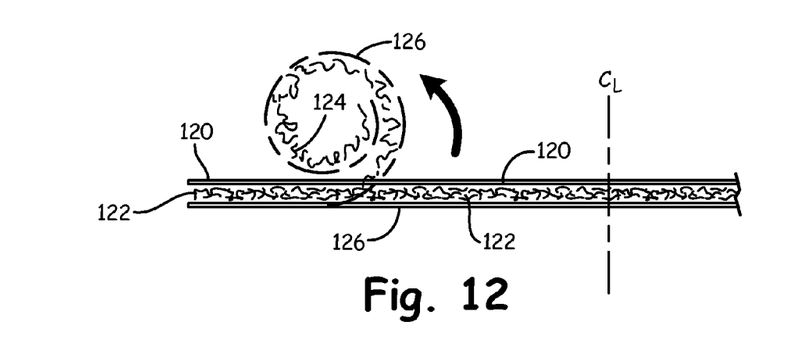
FIG. 12 represents a side schematic view of the absorbent layer of the urine flow barrier shield of FIGS. 10-11 rolled back by the underlying memory retention layer.

The clean-catch embodiment 100 for the urine sample collection device 10 of the present invention is shown in FIGS. 10-12. It comprises a urine flow barrier shield 102, as shown in FIG. 10. It should constitute multiple plies 104, 106, 108, having a substantially flat top surface 110 and an outer perimeter 112. This urine flow barrier shield 102 should be shaped and dimensioned so that its outer perimeter 112 roughly conforms to the interior side walls 28 near the top of the collection vessel 26. Referring to FIG. 5, the perimeter 112 of this barrier shield 102 may be attached to securement lip 114 formed around side walls 28a and 28b within the collection vessel 26. This lip provides a good surface area to which the perimeter of the barrier shield can be secured. Alternatively, a groove formed around the internal circumference of the collection vessel can provide a convenient means for the perimeter edge of the barrier shield to be snap fitted into.

The urine flow barrier shield 102 should be secured to the collection vessel 36 approximately ½-¾ inch below the top of the collection vessel. While this will require a larger surface area for the barrier shield, compared with if it were located further down in the collection vessel, it also protects more of the side walls 28 from becoming contaminated by the initial urine flow which may have the bacteria in it.

As depicted in FIG. 11, the urine flow barrier shield 102 is preferably formed from three layers. The top layer 120 comprises a water-soluble film layer that extends across the entire barrier shield 102. This water-soluble film layer may be made from any suitable material that provides mechanical strength until it disintegrates within approximately two seconds or less after it is contacted by a water-based solution, which forms the principal component in urine. Water-soluble films formed from homogeneous blends of water-soluble polyvinyl alcohol and polyvinyl pyrrolidone wherein both polymers are characterized by having a weight average molecular weight in the range of about 10,000 to 50,000 may be used. Generally, the polymers are blended at weight ratios (on a dry solids basis) of polyvinyl alcohol to polyvinyl pyrrolidone in the range of from about 10:1 to 1:1. The polyvinyl alcohol is partially hydrolyzed polyvinyl acetate having a degree of hydrolysis of less than about 96%. Such a film product is rapidly soluble in cold and warm water, and are clear, transparent, non-tacky, easily handleable, and mechanically strong. They are also stable at both low and high humidity conditions. These type of films are disclosed more fully in U.S. Pat. No. 4,481,326 issued to Sonenstein, which is hereby incorporated by reference. This water-soluble film layer should preferably be about 0.005-0.010 inches in thickness.

Positioned immediately below this water-soluble top layer 120 is an absorbent layer 122. It should be made from a substance comprising fibers or a gel capable of retaining water, while not expanding too much when wet so as not to interfere with its ability to roll upon itself. Super-absorbent sodium polyacrylate gels ground into a powder may be used. Alternatively, natural fibers made from cotton, linen, ramie, animal wool, silk, cellulose, and other suitable materials may be used. Another possibility is synthetic fibers made from suitable absorbent materials like polyester, rayon, acetate, nylon, and fibers comprising polyolefins and polyvinyl alcohol wherein the polyvinyl alcohol has, grafted thereto, hydrophilic polymer moieties. This absorbent material should be capable of readily absorbing any urine that passes through the water-soluble top layer 120. The material should not exceed ¹⁄₁₆ inch in thickness.

Positioned immediately below this absorbent layer 122 and attached directly to the absorbent layer is memory retention film layer 126. This memory retention layer 126 should be formed from a suitable plastic material that has imparted to it the necessary thermoplastic memory properties for curling upon itself to readily recover the curl originally imparted to the material by thermoforming at the time of manufacture. This material should be capable of curling back upon itself (see FIG. 12) within two seconds or less after it is released from its standby, flat position. Suitable polymer materials meeting these criteria include polyethylene terephthalate ("PET") films and mylar films. This memory retention film layer should be about 0.008-0.20 inches in thickness. The "curl-back" properties may be imparted to the film by, e.g., rolling it around a rod under tension and at a temperature around 200° F. for a time period around 15 minutes, although combinations of higher temperatures/lower times or lower temperatures/longer times are possible for providing the desired degree and speed of curl back properties in the film.

As shown in FIGS. 10-11, the absorbent layer 124 secured to the memory retention layer 126 should form an integral two-plied cassette that is divided into separate pieces. Any shape for these pieces will suffice, although a "pie shape" is convenient and therefore preferred. These multiple pieces comprising the absorbent layer/memory retention layer integral combination are positioned next to each other during the stage of manufacture to form the shape of the urine flow barrier shield 102. The water-soluble film layer 122 in a continuous sheet is then laminated to all or a portion of the top surface of the absorbent layer portion of the individual pieces, so that the pieces forming the cassette are held together into an integral whole by the water-soluble film layer. It is important that the water-soluble film layer cover that portion of the barrier shield that is likely to be struck by the falling urine flow when the urine sample collection device 10 is mounted in the toilet, and a patient is urinating from a sitting or standing position.

With the urine flow barrier shield 102 positioned along the top portion of the collection vessel 26 with its perimeter edge 112 secured to the interior lipped surfaces 116 of the collection vessel, the initial flow of urine emitted by the patient will come into contact with the continuous water-soluble layer 122. Due to the material chosen for this water-soluble film layer 122, the initial drops of urine will quickly cause the water-soluble layer to disintegrate. This is the initial urine flow that potentially contains bacteria from around the urinary outlet of the patient's body that must not be introduced into the urine sample pursuant to the clean-catch mid-stream collection method.

Once this water-soluble layer 122 disintegrates, the initial urine drops will come into contact with the absorbent layer 124 of the urine flow barrier shield 102. At the same time, the memory retention layer 126 of the now-separate pie-shaped two-ply cassette pieces will curl back upon themselves, taking the absorbent layer 124 attached to the memory retention layer along to form the roll shown in FIG. 12. In this manner, the two-ply cassette pieces freed from the continuous urine flow barrier shield 102 due to the disintegrated water-soluble layer 122 will become removed from the top surface of the collection vessel 26, and will roll towards the perimeter of the interior surface of the collection vessel where the individual pieces of the barrier shield are still secured. Any bacteria-tainted initial urine drops contained in the adsorbent layers 124 will thereby be removed from the top surface of the collection vessel, and any further mid-stream urine flow that is emitted by the patient can fall directly into the collection vessel to produce an uncontaminated urine sample. This subsequent volume of urine, which should be substantially free of bacterial from around the urinary outlet of the patient's body can now freely flow into the collection vessel 26 and into the sample collection container 40 without coming into contact with the barrier shield 102. In this manner, the clean-catch mid-stream collection embodiment 100 of the present invention permits the patient to quickly and conveniently deliver urine to a toilet in the normal manner with the urine sample collection device 10 contained inside the toilet bowl 14 automatically carrying out the clean-catch mid-stream collection method to produce a urine sample that is substantially free of the bacteria existing around the urinary outlet of the patient's body without any difficult mechanics or timing performed by the patient. The device works in an automatic fashion without any required thought or manipulation by the patient to either the device or the process for providing the flow or urine. This is ideal for children or disabled or elderly patients. Moreover, the exterior of the sample container is free of any splashed urine flow for enhanced cleanliness.

The urine sample collection device 10 of the present invention greatly enhances the sense of privacy and human dignity of the patient without any need for a medical assistant to be personally present in the room while the patient is urinating. This can be reassuring to children and adults. Furthermore, the elderly or disabled individuals can gain a sense of independence by their ability to provide a urine sample without the intrusive intervention of the medical assistant.

Another significant advantage of the urine sample collection device 10 of the present invention is its ability to provide uncontaminated urine samples that reduce the incidence of false positives occurring during urinalysis tests. Such false positive readings for the presence of bacterial strains suggesting urinary tract infections in patients can lead to the over-prescription of antibiotic drugs, and the consequent development within nature of antibiotic-resistant bacterial strains. This is a genuine public health risk.

Figure 13:
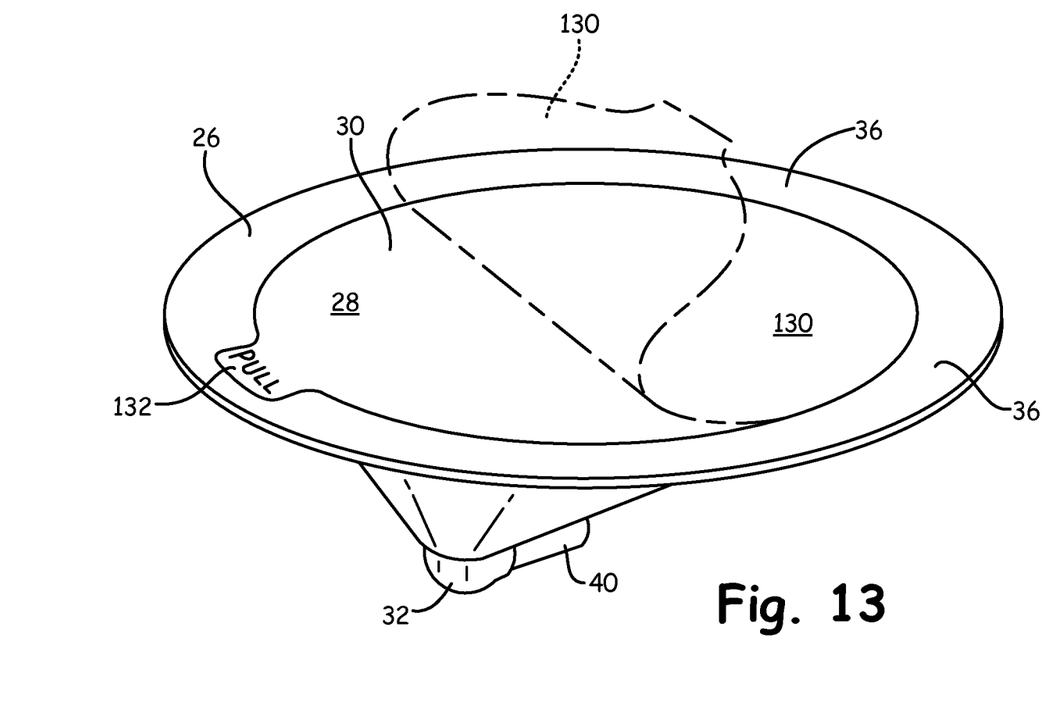
FIG. 13 represents a perspective view of the urine sample collection device with a protective film layer to maintain its sterility before use.

FIG. 13 shows the urine sample collection device 10 of the present invention with a protective film layer 130 secured across the top opening of the collection vessel 26. This layer 130 maintains the sterility of the urine sample collection device 10 before it is used by the patient to deliver the urine sample in order to further protect the integrity and purity of the collected sample. This layer may be made from any suitable polymer film material. It may be peeled off from the top opening of the collection vessel 26 using the leading edge 132.

In a further embodiment of the invention, a design can be added to the interior surface of the side walls 28 of the collection vessel 26. This design element may comprise a picture, cartoon character, animal, or other indicia that would appeal to small children. Alternatively, the design element may be formed from a heat-sensitive ink that is initially invisible, but will become visible when contacted by the warm urine flow. This kind of design element can be used to encourage children to sit on the toilet and provide a urine sample within the urine sample collection device 10 of the present invention.

The following example further illustrates the automatic clean-catch mid-stream collection embodiment of the urine sample collection device of the present invention.

Example I

A four-inch-diameter substrate ring was cut from 0.060-inch-thick ABS plastic to provide a perimeter support for the urine flow barrier shield.

ABS plastic film 0.005 inch thick was rolled around a ½-inch steel rod with aluminum foil separating each wrap of the film. The rolled film assembly was then baked at 200° F. for 15 minutes to create a rolled film memory retention layer that will return to its rolled stated when released from its flat configuration.

3M 77 spray adhesive sourced from 3M Corporation of St. Paul, Minn. was applied to the bottom surface of an absorbent layer made from a single-ply paper towel, which was then laid flat, adhesive side up. The rolled film memory retention layer was then unrolled with its top surface pressed onto the adhesive-coated bottom surface of the absorbent layer with the resulting two-ply cassette pressed under the weight of a flat board to allow the adhesive to completely dry.

A pattern of triangular "leaves" was laid out on the surface of the absorbent layer/memory retention layer cassette oriented so that when cut out, the resulting leaves will roll properly, tip to root of each leaf. The leaves were then cut from the cassette with the root side of each leaf then solvent bonded to the plastic ABS ring to secure the perimeter of the cassette.

Next, the cassette assembly was flipped over with the absorbent layer down. Rolling the leaves out into a flat configuration, they were taped along their back side to hold them in place.

A two-inch-diameter circle constituting a water-soluble film layer was cut from water-soluble paper sourced from Extra Packaging Corp. of Rochester, N.Y. A mask was held over the water-soluble paper and a spray adhesive applied to its bottom surface. The cassette assembly was pressed with its absorbent layer against the spray adhesive on the water-soluble film layer, centering the absorbent layer/memory retention layer assembly on the water-soluble film layer. The adhesive was allowed to dry. The tape was removed from the back side of the leaves since the continuous water-soluble film layer held the leaves of the absorbent layer/memory retention film layer assembly in their flat configuration.

When drops of liquid water acting as a proxy for urine were applied by a straw to the resulting urine flow barrier shield, the water-soluble paper film layer was degraded sufficiently within 0.5-2.0 seconds to allow the now separated absorbent layer/memory retention film layer leaves to be released from their flat configuration, and rolled upon themselves toward their perimeter edges secured to the ABS substrate ring. The first drops of the liquid flow were captured within the absorbent layer during this initial 0.5-2.0 second time period, and safely moved away by the rolled-back memory retention film leaves, so as not to come into contact with the subsequently delivered flow of water droplets.

The experiment was repeated with a 0.010-inch-thick ABS film memory retention layer in combination with all other aspects of the experiment disclosed above. The results were also successful, achieving roll back of the separated absorbent layer/memory retention film layer in a similar 0.5-2.0 second time period.

The results of this experiment suggest that the urine flow barrier shield of the present invention will work to create the automatic clean-catch mid-stream collection process in the urine sample collection device.

The above specification, drawings, and data provide a complete description of the urine sample collection device of the present invention. Since many embodiments of the invention can be made without departing from the spirit and scope of the invention, the invention resides in the claims hereinafter appended.

We claim:

1. A device for collecting a urine sample from a patient, comprising:
    (a) a collection vessel having a top opening, side walls, and an outlet;
    (b) a sample collection container for removably engaging the outlet of the collection vessel;
    (c) a urine flow barrier shield positioned across the top opening of the collection vessel that is automatically removed from at least a substantial portion of the top opening of the collection vessel when a urine flow produced by the patient comes into contact with it during a clean-catch delivery process;
    (d) wherein an initial volume of urine emitted by the patient flowing into the collection vessel is retained within the urine flow barrier shield;
    (e) wherein the subsequent automatic removal of the urine flow barrier shield containing the initial urine volume from at least a substantial portion of the top opening of the collection vessel permits a subsequent mid-stream urine volume emitted by the patient during the clean-catch process to flow into the collection vessel without coming into contact with the initial urine volume;
    (f) wherein the mid-stream urine flow substantially free of any bacterial contained in the initial urine volume flows into the sample collection container to produce the urine sample; and
    (g) wherein the sample collection container may be removed from the outlet of the collection vessel.

2. The urine sample collection device of claim 1, wherein the collection vessel and sample collection container are mounted to a toilet with the collection vessel and attached sample collection container positioned inside the toilet bowl, so that the patient may urinate into the toilet with the urine falling into the urine sample collection device to produce the urine sample.

3. The urine sample collection device of claim 2, wherein the collection vessel and sample collection container are mounted to a seat hingably attached to the toilet, so that raising the seat removes the urine sample collection device from the toilet bowl without the need to manually detach the device from the toilet.

4. The urine sample collection device of claim 1, wherein the urine flow barrier shield comprises multiple-layers.

5. The urine sample collection device of claim 4, wherein the multiple layers comprise a water-soluble film layer, an absorbent layer, and a memory retention film layer attached to the absorbent layer, wherein the absorbent layer retains the initial urine volume, and the memory retention film layer rolls itself and the absorbent layer away from the top opening of the collection vessel to allow the subsequent urine volume to flow into the collection vessel after the water-soluble film layer disintegrates after it is contacted by the initial urine volume.

6. The urine sample collection device of claim 5, wherein the water-soluble film layer comprises a homogeneous blend of water-soluble polyvinyl alcohol and polyvinyl pyrrolidone.

7. The urine sample collection device of claim 5, wherein the absorbent layer comprises a gel or natural or synthetic fiber material.

8. The urine sample collection device of claim 5, wherein the memory retention film layer comprises a plastic material having the necessary thermoplastic memory properties for curling upon itself to readily recover the curl originally imparted to the material by thermoforming at the time of manufacture.

9. The urine sample collection device of claim 8, wherein the plastic material comprises polyethylene terephthalate ("PET") or mylar film.

10. The urine sample collection device of claim 5, wherein the absorbent layer and memory retention film layer portions of the urine flow barrier shield comprise discrete pieces secured together until the continuous water-soluble film layer to which they are laminated disintegrates upon contact by the initial urine volume.

11. The urine sample collection device of claim 5, wherein the water-soluble film layer at least partially disintegrates within two second or less after it is contacted by the initial urine volume.

12. The urine sample collection device of claim 5, wherein the memory retention film layer rolls up within two seconds or less after the water-soluble film layer at least partially disintegrates.

13. The urine sample collection device of claim 1 further comprising anti-splash means for controlling the flow of urine from the collection vessel when the sample collection container is removed from its engagement with the outlet.

14. The urine sample collection device of claim 13, wherein the anti-splash means comprises a valve housing positioned between the collection vessel outlet and the opening of the sample collection container, wherein the valve may be closed once the urine sample is collected within the sample collection container to prevent excess urine contained in the collection vessel from passing through the outlet once the sample collection container is removed from the outlet.

15. The urine sample collection device of claim 13, wherein the anti-splash means comprises a siphon outlet formed within the side wall of the collection vessel with a tube extending therefrom, wherein excess urine contained in the collection vessel is evacuated from the collection vessel through the siphon outlet and tube to prevent it from passing through the outlet once the sample collection container is removed from the outlet.

16. The urine sample collection device of claim 13, wherein the anti-splash means comprises an overflow outlet formed near the bottom of the collection vessel adjacent to a urine collection well in communication with the collection vessel outlet with a wall positioned between the urine collection well and the overflow outlet, wherein the wall regulates the volume of urine that can collect inside the well and pass through the outlet into the sample collection container with any excess urine flowing over the top of the wall through the overflow outlet and out of the collection vessel.

17. The urine sample collection device of claim 16, wherein the volume of the well is slightly less than the open air volume in the sample collection container partially filled with the urine sample, wherein when the urine sample collection device is tipped so that the sample collection container is substantially vertical, the residual urine contained within the well can flow into the sample collection container.

18. The urine sample collection device of claim of claim 1 further comprising a design element placed on the internal side walls of the collection vessel for encouraging child patients to urinate into the collection vessel to produce the urine sample.

* * * * *